United States Patent
Lokhandwala et al.

(10) Patent No.: US 10,738,254 B2
(45) Date of Patent: Aug. 11, 2020

(54) PROCESS AND SYSTEM FOR RECOVERING NATURAL GAS LIQUIDS (NGL) FROM FLARE GAS USING JOULE-THOMSON (J-T) COOLING AND MEMBRANE SEPARATION

(71) Applicants: Kaaeid A. Lokhandwala, Fremont, CA (US); Sachin Joshi, Mountain View, CA (US)

(72) Inventors: Kaaeid A. Lokhandwala, Fremont, CA (US); Sachin Joshi, Mountain View, CA (US)

(73) Assignee: Membrane Technology and Research, Inc., Newark, CA (US)

( * ) Notice: Subject to any disclaimer, the term of this patent is extended or adjusted under 35 U.S.C. 154(b) by 183 days.

(21) Appl. No.: 16/055,874

(22) Filed: Aug. 6, 2018

(65) Prior Publication Data

US 2018/0346833 A1 Dec. 6, 2018

Related U.S. Application Data (62) Division of application No. 15/145,143, filed on May 3, 2016, now Pat. No. 10,059,895.

(Continued)

(51) Int. Cl.
*B01D 63/00* (2006.01)
*B01D 3/00* (2006.01)
(Continued)

(52) U.S. Cl.
CPC ............. *C10L 3/101* (2013.01); *C07C 7/005* (2013.01); *C07C 7/04* (2013.01); *C07C 7/12* (2013.01); *C07C 7/144* (2013.01); *C07C 7/20* (2013.01); *C10G 5/06* (2013.01); *C10G 70/045* (2013.01); *C10L 3/106* (2013.01); *C10L 3/107* (2013.01); *F25J 3/0635* (2013.01); *C10G 2300/1025* (2013.01); *C10G 2300/1033* (2013.01); *C10L 2200/0461* (2013.01); *C10L 2270/04* (2013.01); *C10L 2290/06* (2013.01);

(Continued)

(58) Field of Classification Search
None
See application file for complete search history.

(56) References Cited

U.S. PATENT DOCUMENTS 5,352,272 A 10/1994 Moll et al.
5,501,722 A 3/1996 Toy et al.
(Continued)

FOREIGN PATENT DOCUMENTS

AU WO2008095258 A1 8/2008

*Primary Examiner* — Philip Y Louie
(74) *Attorney, Agent, or Firm* — Stinson LLP (57) ABSTRACT

A process and system for recovering natural gas liquids (NGL) using a combination of J-T cooling and membrane separation. The process involves compressing, separating, and cooling a flare gas stream comprising at least methane and $C_{3+}$ hydrocarbons prior to being introduced to a J-T valve. The cooled stream exiting the J-T valve is further separated, producing a NGL product stream and an uncondensed gas stream. The uncondensed gas stream is directed to a membrane separation step, which results in a $C_{3+}$ hydrocarbon enriched stream and a $C_{3+}$ hydrocarbon depleted stream. The $C_{3+}$ hydrocarbon enriched stream may be recycled back to the process to recover more NGL.

26 Claims, 6 Drawing Sheets

Related U.S. Application Data (60) Provisional application No. 62/156,491, filed on May 4, 2015.

(51) Int. Cl.

| | | |
|---|---|---|
| *C10L 3/10* | (2006.01) | |
| *C10G 70/04* | (2006.01) | |
| *C10G 5/06* | (2006.01) | |
| *C07C 7/00* | (2006.01) | |
| *C07C 7/04* | (2006.01) | |
| *C07C 7/12* | (2006.01) | |
| *C07C 7/144* | (2006.01) | |
| *C07C 7/20* | (2006.01) | |
| *F25J 3/06* | (2006.01) | |

(52) U.S. Cl.
CPC ....... *C10L 2290/08* (2013.01); *C10L 2290/10* (2013.01); *C10L 2290/46* (2013.01); *C10L 2290/541* (2013.01); *C10L 2290/543* (2013.01); *C10L 2290/548* (2013.01)

(56) References Cited

U.S. PATENT DOCUMENTS

| | | |
|---|---|---|
| 5,685,170 A | 11/1997 | Sorensen |
| 5,755,855 A | 5/1998 | Baker et al. |
| 5,762,685 A | 6/1998 | Baker et al. |
| 6,053,965 A | 4/2000 | Lokhandwala |
| 6,128,919 A | 10/2000 | Daus et al. |
| 6,190,536 B1 * | 2/2001 | Lokhandwala ........... C07C 4/06 208/100 |
| 8,381,543 B2 | 2/2013 | Ransbarger et al. |
| 2009/0299120 A1 | 12/2009 | Geers et al. |
| 2012/0096895 A1 | 4/2012 | Patel et al. |
| 2013/0014643 A1 | 1/2013 | Lokhandwala et al. |
| 2014/0216104 A1 | 8/2014 | Imaev et al. |
| 2014/0366577 A1 | 12/2014 | Zubrin et al. |

* cited by examiner

Figure 1
(not in accordance with the invention)

PROCESS AND SYSTEM FOR RECOVERING NATURAL GAS LIQUIDS (NGL) FROM FLARE GAS USING JOULE-THOMSON (J-T) COOLING AND MEMBRANE SEPARATION

CROSS-REFERENCE TO RELATED APPLICATIONS

This application is a divisional and claims the benefit of U.S. application Ser. No. 15/145,143, filed on May 3, 2016, and now issued as U.S. Pat. No. 10,059,895 on Aug. 28, 2018, which claims the benefit of U.S. Provisional Patent Application No. 62/156,491, filed on May 4, 2015, which is hereby incorporated by reference in its entirety.

FIELD OF THE INVENTION

The invention relates to a process and system for recovering natural gas liquids (NGL). More specifically, the invention relates to treating a flare gas stream using Joule-Thomson (J-T) cooling and gas separation membranes for recovering NGL and methane.

BACKGROUND OF THE INVENTION

The growth in petroleum and natural gas processing around the world has led to an increased awareness about the amount of gas being flared into the atmosphere. Not only does flaring pose an environmental concern due to the amount of carbon dioxide being released (some 400 million tons worth), but it also represents a major waste of natural resources and money. In North Dakota, for example, it is estimated that about $1 billion worth of $C_{3+}$ hydrocarbons, also known as natural gas liquids, are flared per year rather than being recovered on-site. Globally, the number is estimated to be close to $20 billion.

The lack of investment in infrastructure needed to handle large amounts of natural gas or associated gas from oil reservoirs contributes to the issue of flare waste. The building of gas pipelines is usually given lesser priority over the development of more lucrative oil wells. Additionally, these oil wells are typically in remote locations where there is no local market for sales gas. While legislative measures are being taken by governments around the world to promote the use of flare-reduction technology, the systems currently in place are large, costly and energy-intensive.

Figure 1:
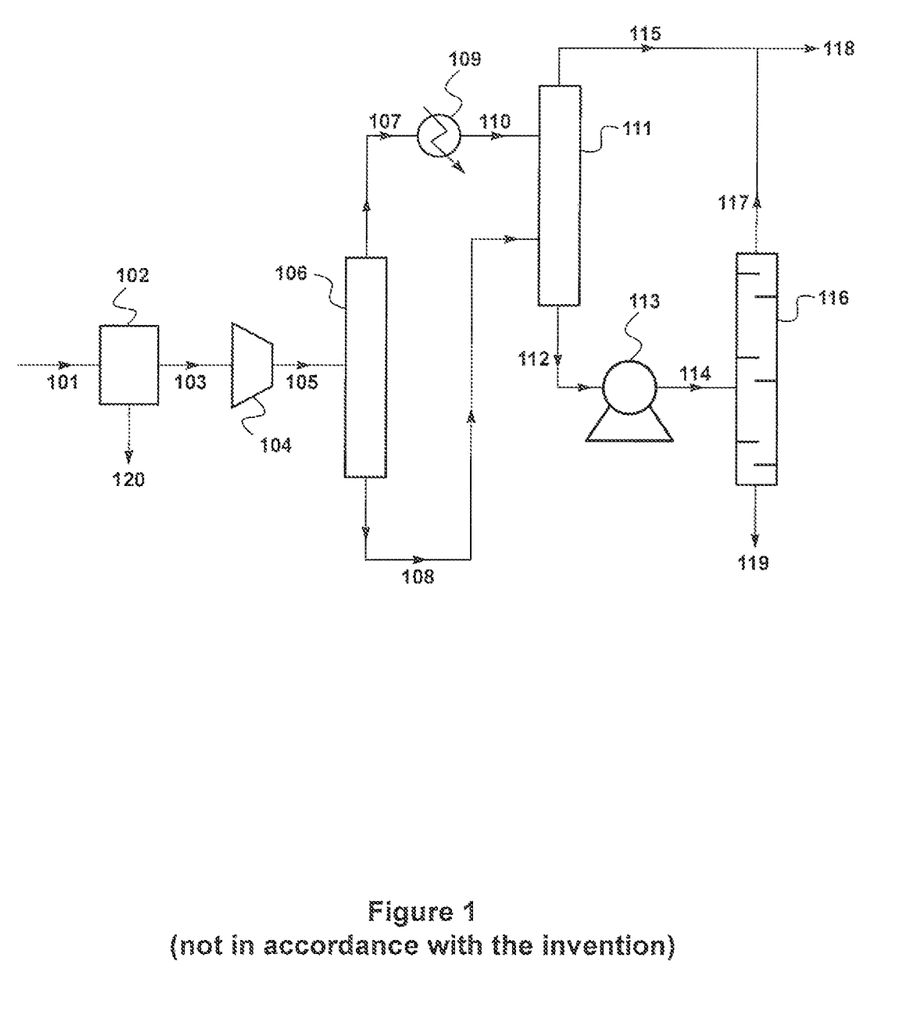
FIG. 1 is a schematic drawing showing a conventional NGL recovery process using refrigeration and without membrane separation (not in accordance with the invention).

A conventional way to recover $C_{3+}$ hydrocarbons from flare gas is shown in FIG. 1.

Referring to this figure, a relatively low-pressure flare gas, 101, comprising mostly of methane and $C_{3+}$ hydrocarbons, but also including ethane, nitrogen, acid gases, and water vapor, is first sent to a dehydration unit, 102, to remove water-enriched stream 120. Any water or hydrates present in the flare gas must be removed prior to refrigeration in order to avoid fouling downstream processes that operate at below freezing temperatures. A dehydrated gas stream, 103, is withdrawn from dehydration unit, 102, and is passed to a compressor, 104, which produces a compressed stream, 105.

Next, compressed stream 105 is directed to a first separator, 106. The first separation unit is typically a gas-liquid phase separator or the like that separates the incoming compressed stream into a first hydrocarbon liquid stream, 108, containing $C_{3+}$ hydrocarbon and a first gas stream, 107, depleted in $C_{3+}$ hydrocarbons.

The first gas stream, 107, is then sent to a refrigeration process, 109, in order to condense additional amounts of $C_{3+}$ hydrocarbons. The refrigeration process, 109, is typically operated by further compression in a second compression step, then chilled down to about −20° C. or −40° C., depending on pressure, or by cooling under cryogenic conditions to about −100° C. Typically, external refrigerants are used to cool the natural gas stream, and then, an expansion turbine is used to rapidly expand the chilled gases, thereby causing significant further cooling. This rapid temperature drop condenses $C_{3+}$ hydrocarbons in the gas stream, while maintaining methane in gaseous form. However, turboexpanders require a large capital investment and, depending on the process, may not be an economically viable option.

Alternatively, cooling may be achieved by using Joule-Thomson expansion across a pressure-reducing valve. However, this method is not effective to achieve significant cooling unless the incoming gas is at very high pressure, so that a very large pressure differential across the valve can be obtained.

After undergoing refrigeration, the cooled gas stream, 110, is sent to a second separation unit, 111. First hydrocarbon liquid stream 108 is also sent to this unit. The second separation unit, 111, separates incoming streams 108 and 110 into a second hydrocarbon liquid stream, 112, which is enriched in $C_{3+}$ hydrocarbons, and a second gas stream, 115, that is depleted in $C_{3+}$ hydrocarbons.

The second hydrocarbon liquid stream, 112, is passed to a blower (or compressor), 113, before entering a distillation column, 116. The distillation column, 116, is typically a deethanizer or demethanizer, from which a third hydrocarbon liquid stream, 119, enriched in $C_{3+}$ hydrocarbons, is removed as a bottoms product.

A third gas stream, 117, which is depleted in $C_{3+}$ hydrocarbons, is removed from the top of distillation column 116 and is eventually mixed with second gas stream 115 to produce mixed gaseous stream 118, which may be flared or used as fuel or sales gas.

A variety of NGL recovery processes are known in the literature and are described in detail, below.

U.S. Pat. No. 5,352,272 to Moll et al. describes processes for operating certain glassy membranes selective for carbon dioxide over methane at temperatures of 5° C. or below. The patent shows an example, Example 10, in which self-refrigeration of the feed gas to the desired operating temperature is provided by Joule-Thomson cooling.

Co-owned U.S. Pat. No. 5,501,722 to Toy et al. discloses a membrane having a selective layer comprising poly(trimethylsilylpropyne) that is selectively permeable to $C_{3+}$ hydrocarbons over methane. The membrane may be used in NGL recovery from refinery gases or off gases from the petrochemical industry.

U.S. Pat. No. 5,685,170 to Sorenson et al. discloses an NGL recovery process using an absorber employed upstream of an expansion device, such as a turboexpander or a J-T valve, wherein the cooled vapor streams from the absorber are combined with the cooled and expanded vapor stream of a downstream distillation column. While such configurations advantageously make use of the pressure in the feed gas, a gas dehydration unit must be installed for the cryogenic expander operation, and residue gas in such plants needs to be recompressed which negates any cost or energy savings.

Co-owned U.S. Pat. No. 6,053,965 to Lokhandwala et al. describes a fuel gas conditioning process that may be used to produce an NGL product. According to the general process disclosed in the '965 patent, a portion of gas from a high-pressure gas stream is withdrawn, then cooled by passing the portion through a heat-exchange step in heat-exchanging relationship against a membrane residue stream.

The portion is then separated into a liquid phase comprising $C_{3+}$ hydrocarbons (NGL) and a gas phase depleted in $C_{3+}$ hydrocarbons. The gas phase is then passed across the feed side of a membrane unit containing a membrane selective for $C_{3+}$ hydrocarbons over methane. A $C_{3+}$-depleted membrane residue stream is then withdrawn from the feed side and passed back to the heat exchange step. A $C_{3+}$-enriched permeate stream is withdrawn from the permeate side. The membrane residue stream may optionally be used as combustion fuel for a prime mover.

U.S. PGPUB 2012/0096895 to Patel et al. teaches a process using a combination of expansion, separation, and compression sequences to recover NGL without the need for a demethanizer column. To provide expansion cooling, the process uses J-T valves or turboexpanders.

While improvements have been made in NGL recovery processes, the current technology still relies on the use of expensive refrigeration/cryogenic equipment. Given the need to develop technology for reducing flare gas waste and the current costs of prior art processes, it would be desirable to have a cheaper and more efficient process for enhanced recovery of NGL.

SUMMARY OF THE INVENTION

The present invention relates to an improved process and system for treating a flare gas stream in order to recover NGL and methane. The process usually has only one step involving moving equipment, specifically a compressor, which produces driving force for both the J-T cooling and membrane separation steps. This combination replaces the second compressor and refrigeration/cryogenic condensation steps of current systems. The invention results in a process and system that recovers NGL efficiently, uses less energy, is cheaper, and is environmentally friendlier than conventional processes.

As with the non-membrane processes described previously, it will generally be desirable to dehydrate the flare gas stream at a convenient point before it enters the cooling/condensation steps of the new process. Any type of dehydration unit known in the art may be used. A molecular sieve is preferred to reduce the water content of the stream to essentially zero. Alternatively, a hydrate-inhibiting chemical, such as methanol, may be injected into the gas stream prior to the cooling/condensation steps.

In its most basic embodiment, the invention is a process for treating a flare gas stream, the flare gas stream comprising at least methane and $C_{3+}$ hydrocarbons, and the process comprising the following steps:

(a) compressing the flare gas stream with a compressor to produce a compressed gas stream;

(b) separating the compressed stream in a first separation unit to produce a first hydrocarbon liquid stream enriched in $C_{3+}$ hydrocarbons relative to the compressed stream and first gas stream depleted in $C_{3+}$ hydrocarbons relative to the compressed stream;

(c) cooling said first gas stream depleted in $C_{3+}$ hydrocarbons in a heat-exchange unit to produce a cooled gas stream;

(d) directing the cooled gas stream through a Joule-Thomson valve to produce an expanded gas stream;

(e) routing the first hydrocarbon liquid stream and the expanded gas stream to a second separation unit to produce a second hydrocarbon liquid stream enriched in $C_{3+}$ hydrocarbons relative to the expanded gas stream and a second gas stream depleted in $C_{3+}$ hydrocarbons relative to the expanded gas stream;

(f) heating the second gas stream depleted in $C_{3+}$ hydrocarbons by heat exchange against the first gas stream in the heat-exchange unit of step (c) to generate a heated gas stream;

(g) passing the heated gas stream as a feed stream across a membrane selective for methane over $C_{3+}$ hydrocarbons to produce a permeate stream enriched in methane and a residue stream depleted in methane as compared to the heated gas stream; and (h) recycling the residue stream depleted in methane back to the flare gas stream prior to step (a).

The process of the invention involves first compressing a low pressure flare gas stream with a compressor in step (a). The flare gas stream should be at a high pressure in order to attain sufficient downstream expansion. Preferably, the process only uses one compressor unit in this step, but a compressor train comprising more than one unit may be used. Preferably, step (a) should raise the pressure of the flare gas stream to a pressure in the range of 500-1,500 psia.

In step (b), the compressed stream is separated into a liquid condensate enriched in $C_{3+}$ hydrocarbons and a first gas stream (or off-gas) depleted in $C_{3+}$ hydrocarbons. Typically, the compressed stream is passed through the aftercooler of the compressor, then through one or more knockout vessels or phase separators, thereby producing a first hydrocarbon liquid stream and a first gas stream.

The first gas stream is depleted in $C_{3+}$ hydrocarbons and is sent for cooling in heat-exchange step (c). The first gas stream may be cooled against any available streams. Preferably, the heat exchange occurs at least between the first gas stream, which is typically at a temperature of about 40° C., and the second gas stream from step (e), which is typically at a temperature of about −5° C., for example.

In step (d), the cooled first gas stream is directed through a J-T valve to produce an expanded gas stream. The J-T valve chills the uncondensed gas stream by expansion. By way of example, expansion through the valve reduces the cooled gas stream pressure by about 2, 3 or 4 fold, with a corresponding reduction in temperature, preferably to below 0° C.

After passing through the J-T valve, the expanded gas stream is sent in step (e) to a second separation unit, which produces a second gas stream depleted in $C_{3+}$ hydrocarbons and a second hydrocarbon liquid stream enriched in $C_{3+}$ hydrocarbons. In certain embodiments, the second separation unit may again be a simple gas-liquid phase separator of the type described for use in the first step. In other embodiments, it may be a distillation column, typically a demethanizer or deethanizer that stabilizes the NGL product by removing additional light gases.

In step (f), the second gas stream depleted in $C_{3+}$ hydrocarbons is passed through the heat exchange unit of step (c) where the stream is heated by heat exchange against the first gas stream produced in step (b). Advantageously, because the second gas stream is at a cooler temperature than that of the first gas stream, passing the second gas stream through a heat exchanger allows the first gas stream to be further cooled prior to entering the J-T valve.

The heated gas stream is then sent as a feed stream to the membrane of step (g). In certain embodiments, the membrane is selectively permeable to methane, thus resulting in a methane-enriched permeate stream and a methane-depleted residue stream as compared to the feed stream. Membranes for use in this step may comprise any material suitable for preferentially permeating methane over $C_{3+}$ hydrocarbons, but will typically include a selective layer that comprises a glassy polymeric material.

In certain embodiments, the membrane comprises a polymer having the formula:

where x and y represent the relative proportions of the dioxole and the tetrafluoroethylene blocks, such that x+y=1, and where x>0 and y>0.

In other embodiments, the membrane separation of step (g) is preferentially selective to $C_{3+}$ hydrocarbons over methane, thus resulting in a $C_{3+}$-enriched permeate stream and a $C_{3+}$-depleted residue stream as compared to the feed stream. Thus, in some aspects, the invention is a process for treating a flare gas stream, the flare gas stream comprising at least methane and $C_{3+}$ hydrocarbons, and the process comprising the following steps:

(a) compressing the flare gas stream with a compressor to produce a compressed gas stream;

(b) separating the compressed stream in a first separation unit into a first hydrocarbon liquid stream enriched in $C_{3+}$ hydrocarbons relative to the compressed stream and a first gas stream depleted in $C_{3+}$ hydrocarbons relative to the compressed stream;

(c) cooling said first gas stream depleted in $C_{3+}$ hydrocarbons in a heat-exchange unit to produce a cooled gas stream;

(d) directing the cooled gas stream through a Joule-Thomson valve to produce an expanded gas stream;

(e) routing the first hydrocarbon liquid stream and the expanded gas stream to a second separation unit to separate a second hydrocarbon liquid stream enriched in $C_{3+}$ hydrocarbons relative to the expanded gas stream and a second gas stream depleted in $C_{3+}$ hydrocarbons relative to the expanded stream;

(f) heating the second gas stream depleted in $C_{3+}$ hydrocarbons by heat exchange against the first gas stream in the heat-exchange unit of step (c) to generate a heated gas stream;

(g) passing the heated gas stream as a feed stream across a membrane selective in favor of $C_{3+}$ hydrocarbons over methane to produce a permeate stream enriched $C_{3+}$ hydrocarbons relative to the heated gas stream and a residue stream depleted in $C_{3+}$ hydrocarbons relative to the heated gas stream; and (h) recycling the permeate stream enriched in $C_{3+}$ hydrocarbon back the flare gas stream prior to step (a).

Membranes used in step (g) of this embodiment may comprise any material suitable for preferentially permeating $C_{3+}$ hydrocarbons over methane, but will typically include a selective layer that comprises a rubbery elastomeric polymeric material.

Regardless of whether the membrane is methane- or $C_{3+}$ hydrocarbon-selective, the $C_{3+}$-enriched stream is recycled to a point in the process upstream of step (a). The recycling of this stream back to the process allows for additional NGL recovery. The methane-enriched stream/$C_{3+}$-depleted stream withdrawn from the membrane separation step may be sold as a sales gas, or advantageously, be sent as fuel to a fuel user, such as power generation equipment or a gas engine that drives the compressor in step (a).

In certain embodiments, the process described above may also comprise a further separation unit. This third separation unit is used to further remove any non-$C_{3+}$ hydrocarbon components from the second hydrocarbon liquid stream. Thus, the process of the present invention may further comprise the steps of:

(i) directing the second hydrocarbon liquid stream to a third separation unit to produce a third hydrocarbon liquid stream enriched in $C_{3+}$ hydrocarbons relative to the second hydrocarbon liquid stream and third gas stream depleted in $C_{3+}$ hydrocarbons relative to the second hydrocarbon liquid stream; and (j) sending the third gas stream to combine with the heated gas stream of step (f) prior to step (g).

In preferred embodiments, the third separation unit is a distillation column, such as a demethanizer, deethanizer or the like, in which the NGL liquid stream from the second separation step is stabilized. The overhead stream from this column may be combined with the heated gas stream and directed as additional feed to the membrane separation of step (g). The bottoms stream from the column is the stabilized NGL product.

In a further embodiment, the invention relates to a system for performing the process of the invention.

It is to be understood that the above summary and the following detailed description are intended to explain and illustrate the invention without restricting it in scope.

DETAILED DESCRIPTION OF THE INVENTION

The term "natural gas liquids" refers to hydrocarbon liquids recovered from natural gas and including $C_{3+}$ hydrocarbons.

The terms "$C_{3+}$ hydrocarbon" and "heavier hydrocarbon" mean a hydrocarbon having at least three carbon atoms.

The terms "lighter" and "leaner" mean reduced in $C_{3+}$ hydrocarbon content.

The invention relates to an improved process for recovering NGL from a flare gas comprising at least methane and $C_{3+}$ hydrocarbons. The process uses J-T cooling through an expansion valve in combination with membranes having a selective layer comprising either a glassy or rubbery polymer that is selective for methane or $C_{3+}$ hydrocarbons, respectively. The process provides that a stream withdrawn from the membrane enriched in $C_{3+}$ hydrocarbons may be recycled to recover more NGL. The process can be used to replace existing processes at field facilities or gas processing plants that use expensive turboexpanders and mechanical refrigeration operations to recover NGL.

Figure 2:
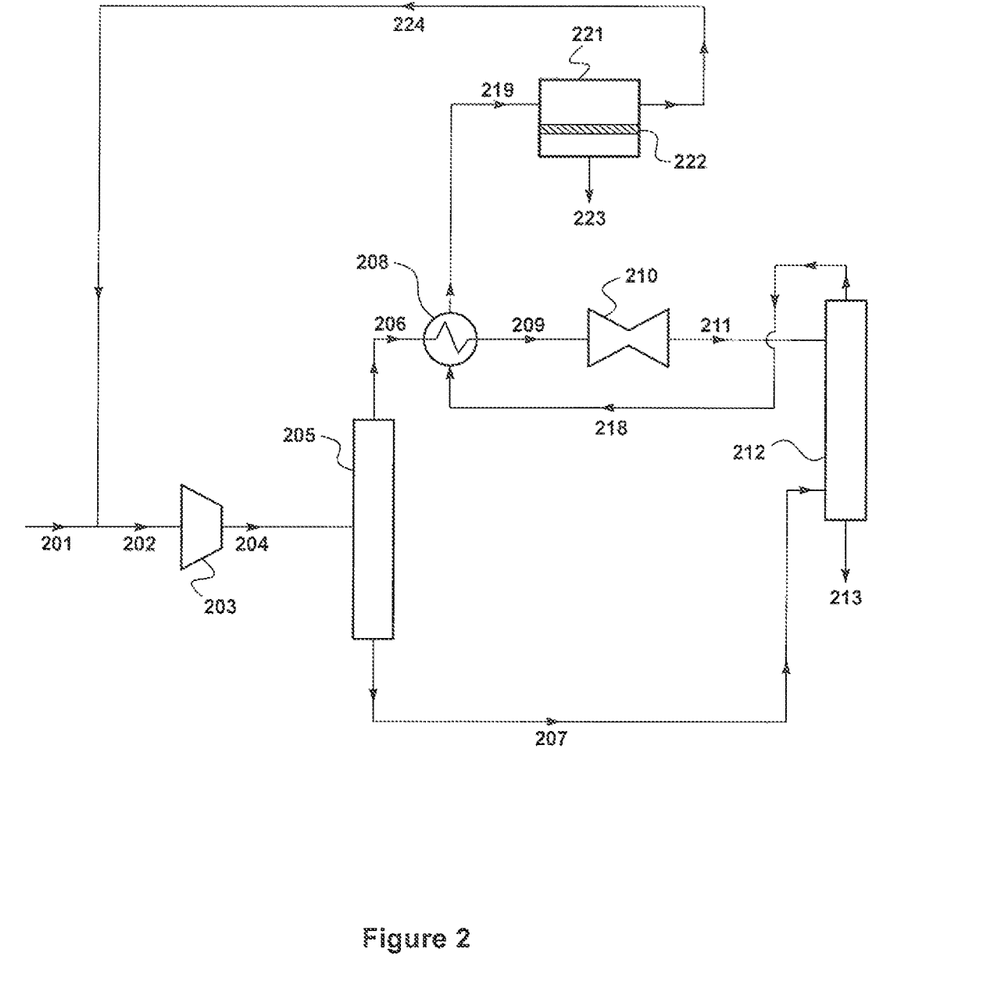
FIG. 2 is a schematic drawing showing a basic embodiment of the invention using a membrane having a selective layer comprising a glassy polymer.

A basic process according to the invention is shown in FIG. 2.

It will be appreciated by those of skill in the art that FIG. 2 and the other figures showing process schemes herein are very simple block diagrams, intended to make clear the key unit operations of the embodiment processes of the invention, and that actual process trains may include many additional steps of standard type, such as heating, chilling, compressing, condensing, pumping, various types of separation and/or fractionation, as well as monitoring of pressures, temperatures, flows, and the like. It will also be appreciated by those of skill in the art that the details of the unit operations may differ from process to process.

A flare gas, 201, is combined with a recycled $C_{3+}$ hydrocarbon stream, 224, to produce a gas mixture stream, 202. The flare gas typically contains at least methane and $C_{3+}$ hydrocarbons and may contain additional gas components, such as nitrogen and acid gases, and in some cases, water vapor.

Gas mixture stream 202 is routed to compression step, 203, the goal of which is to compress the stream to a pressure in which the gas mixture may be partially condensed in the subsequent process steps. The compression step may be carried out using compressor equipment of any convenient types, and may be performed in more than two steps or in a compression train of multiple sub-steps, depending on the degree of compression needed.

The stream emerging from compression step 203 is a compressed stream, 204. This stream is sent through the compressor aftercooler (not shown in the figure) to a first separation step, 205. This step separates gas from liquids in a phase separator, a knock-out drum or the like to yield a first hydrocarbon liquid stream, 207, enriched in $C_{3+}$ hydrocarbons and a first gas stream, 206, depleted in $C_{3+}$ hydrocarbons. In this step, lighter hydrocarbons are removed from heavier hydrocarbons, which otherwise could not pass through the subsequent heat exchange and J-T expansion steps without clogging or fouling these operations.

Stream 206 is then directed to a heat exchange step, 208. Because stream 206 is at a relatively warm temperature, such as about 40° C., it is desirable that the stream be cooled prior to entering a J-T expansion step, 210. Pre-chilling the natural gas before it flows into the J-T valve results in a considerably lower temperature and produces significantly more natural gas liquids. Cooling of stream 206 may be accomplished in any way, but preferably by heat exchange against other on-site process streams. In FIG. 2, the heat exchange occurs between cooled overhead stream, 218, and stream, 206.

Cooled gas stream, 209, passes to a J-T expansion step, 210. Expansion of the gas at the J-T valve results in significant cooling, and brings expanded gas stream, 211, to a temperature at which a substantial fraction of the $C_{3+}$ hydrocarbon content will condense out of the stream. Preferably this temperature is below 0° C., and in the range 0 to −10° C. Very cold temperatures are not required, as any uncondensed gas fraction will be further treated in the subsequent membrane separation step. While sub-zero temperatures are preferred, it can be seen from the Examples section that some useful NGL recovery is possible even at relatively high temperatures after expansion, such as 10° C. or even above.

In a next step, the expanded gas stream, 211, and the first hydrocarbon liquid stream, 207, are sent to a second separation step, 212. This second separation yields a second hydrocarbon liquid stream, 213, enriched in $C_{3+}$ hydrocarbons and a second gas stream, 218, depleted in $C_{3+}$ hydrocarbons. In FIG. 2, the second separation step, 212, may be a distillation column or a simple phase separator.

The second gas stream, 218, is removed from the second separation step, 212, and sent back to the heat-exchange step, 208, where it is used to cool incoming stream 206. Heat transfer between streams 218 and 208 produces warmed stream, 219 and cooled stream 209. Heating of stream 218 in this way prior to membrane separation is beneficial in that it helps to alleviate any condensation of heavier hydrocarbons on the membrane surface during the following membrane separation step, 221.

Stream 219 is sent as a feed stream to a membrane separation step, 221. Any membrane with suitable performance properties may be used in the membrane separation step. The membrane may take the form of a homogeneous film, an integral asymmetric membrane, a multi-layer composite membrane, a membrane incorporating a gel or liquid layer or particulates, or any other form known in the art.

Membranes for use in separation step 221 may comprise a selective layer, 222, that may comprise any polymer that will preferentially permeate methane over $C_{2+}$ hydrocarbons. Preferred membrane materials are glassy polymers, such as, for example and without limitation, polyamides, polyimides, polysulfones, polyvinyl alcohol, polypropylene oxide, cellulose derivatives, polyvinylidene fluoride and polymers having repeating units of fluorinated dioxoles, fluorinated dioxolanes, and fluorinated cyclically polymerizable alkyl ethers. Particularly preferred membranes have selective layers made from a hydrophobic fluorinated glassy polymer or copolymer.

Specific most preferred materials are copolymers of tetrafluoroethylene with 2,2,4-trifluoro-5-trifluoromethoxy-1,3-dioxole having the structure:

where x and y represent the relative proportions of the dioxole and the tetrafluoroethylene blocks, such that x+y=1.

Such materials are available commercially from Solvay Solexis, Thorofare, N.J., under the trade name Hyflon® AD. Different grades are available varying in proportions of the dioxole and tetrafluoroethylene units, with fluorine:carbon ratios of between 1.5 and 2, depending on the mix of repeat units. For example, grade Hyflon® AD 60 contains a 60:40 ratio of dioxole to tetrafluoroethylene units, has a fractional free volume of 0.23, a density of 1.93 $g/cm^3$ and a glass transition temperature of 121° C., and grade Hyflon® AD 80 contains an 80:20 ratio of dioxole to tetrafluoroethylene units, has a fractional free volume of 0.23, a density of 1.92 $g/cm^3$ and a glass transition temperature of 134° C.

The fluorinated polymer is preferably heavily fluorinated, by which we mean having a fluorine:carbon ratio of atoms in the polymer of at least about 1:1. Most preferably, the polymer is perfluorinated Other specific highly preferred materials include the set of polyperfluoro (alkenyl vinyl ethers) including polyperfluoro (allyl vinyl ether) and polyperfluoro (butenyl vinyl ether) that are cyclically polymerizable by the formation of repeat units of ether rings with five or six members in the ring.

A particular preferred material of this type has the structure:

where n is a positive integer.

This material is available commercially from Asahi Glass Company, of Tokyo, Japan, under the trade name Cytop®. Cytop® has a fractional free volume of 0.21, a glass transition temperature of 108° C., and a fluorine:carbon ratio of 1.7.

A third group of materials that is believed to contain useful selective layer materials under some circumstances is:

where x and y represent the relative proportions of the dioxole and the tetrafluoroethylene blocks, such that x+y=1.

Such materials are available commercially from DuPont of Wilmington, Del., under the tradename Teflon® AF.

The polymer chosen for the selective layer can be used to form films or membranes by any convenient technique known in the art, and may take diverse forms. If super-glassy membranes are used, they may be formed as integral asymmetric or composite membranes.

Because the polymers are glassy and rigid, an unsupported film, tube, or fiber of the polymer is usable as a single-layer membrane. However, single-layer films will normally be too thick to yield acceptable transmembrane flux however, and, in practice, the separation membrane usually comprises a very thin selective layer that forms part of a thicker structure, such as an integral asymmetric membrane or a composite membrane.

The preferred form is a composite membrane. Modern composite membranes typically comprise a highly permeable, but relatively non-selective, support membrane that provides mechanical strength, coated with a thin selective layer of another material that is primarily responsible for the separation properties. Typically, but not necessarily, such a composite membrane is made by solution-casting the support membrane, then solution-coating the selective layer. Preparation techniques for making composite membranes of this type are well known.

The membranes may be manufactured as flat sheets or as fibers and housed in any convenient module form, including spiral-wound modules, plate-and-frame modules, and potted hollow fiber modules. The making of all these types of membranes and modules is well-known in the art. Flat-sheet membranes in spiral-wound modules are the most preferred choice.

The membrane separation steps disclosed herein may be carried out using a single membrane module or a bank of membrane modules or an array of modules. A single unit or stage containing on or a bank of membrane modules is adequate for many applications. If either the residue or permeate stream, or both, requires further $C_{3+}$ hydrocarbon removal, it may be passed to a second bank of membrane modules for a second processing step. Such multi-stage or multi-step processes, and variants thereof, will be familiar to those of skill in the art, who will appreciate that the membrane separation step may be configured in many possible ways, including single-stage, multistage, multistep, or more complicated arrays of two or more units, in serial or cascade arrangements.

The membrane separation steps disclosed herein can be operated by any mechanism that provides a driving force for transmembrane permeation. Most commonly, this driving force is provided by maintaining a pressure difference between the feed and permeate sides, or by sweeping the permeate side continuously with a gas that dilutes the permeating species, both of which techniques are well known in the membrane separation arts.

Referring back to FIG. 2, a residue stream, 224, which is depleted in methane and enriched in $C_{3+}$ hydrocarbons relative to stream 219, is withdrawn from the feed side of the membrane. Residue stream 224 represents a significant source of $C_{3+}$ hydrocarbons that may be recovered if recycled back to the process. Thus, in a preferred embodiment, residue stream 224 is sent back to the process prior to compression step 203.

A permeate stream, 223, enriched in methane compared to stream 219, is withdrawn from the permeate side of the membrane. Permeate stream 223 represents a source of fuel gas that may be used for on-site fuel users. The fuel user is typically a gas engine or other device used to generate power or drive a compressor, such as the compressor in compression step 203, but may alternatively be used for a generator set. The gas stream being treated using the process of the invention is typically a high-pressure gas stream created by a compressor driven by a gas engine, and one aspect of the process typically involves using the membrane permeate stream enriched in methane as fuel for the gas engine. The membrane permeate stream may be routed to the fuel user through a pressure control valve at an appropriate pressure point.

Figure 3:
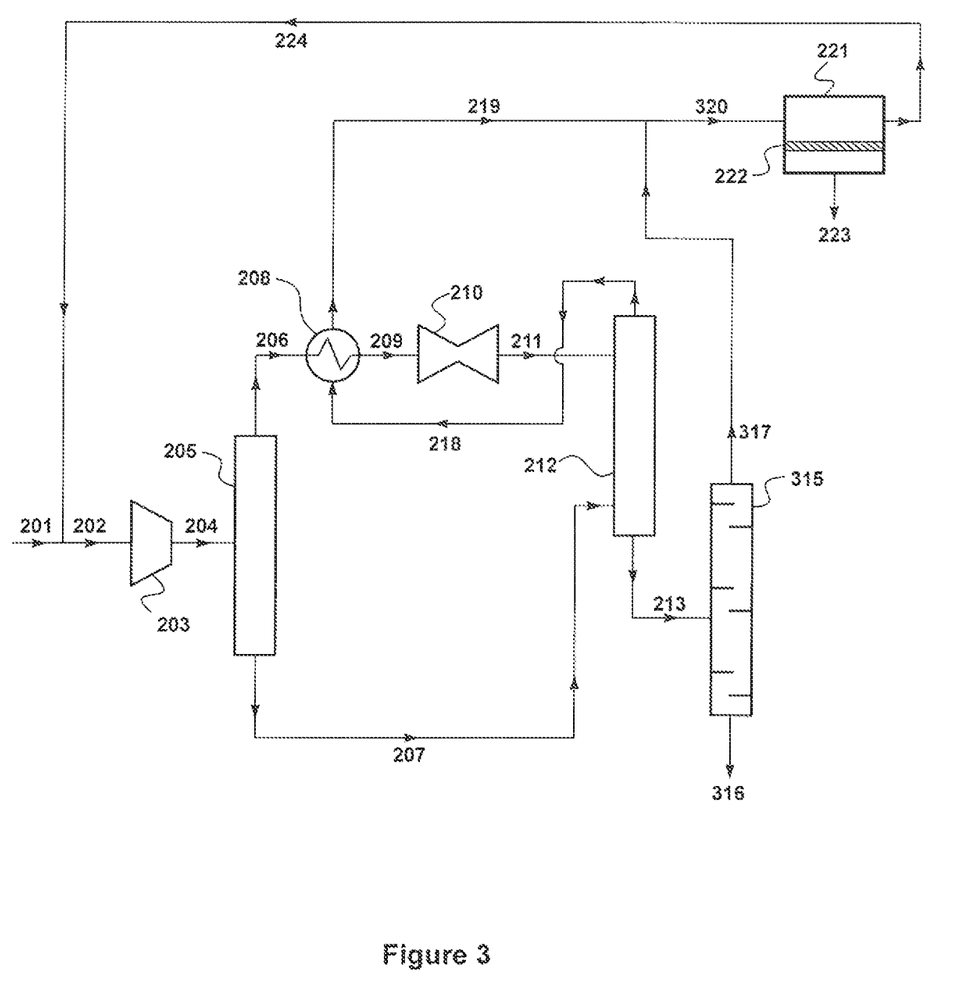
FIG. 3 is a schematic drawing showing an alternative embodiment of the invention of FIG. 2 with the addition of a third separation unit.

Another embodiment of the NGL recovery process is shown in FIG. 3. This embodiment is similar to that of FIG. 2 with the addition of a third separation step, 315.

The principal purpose of step 315 is to stabilize the raw NGL stream to reduce or remove light hydrocarbons that may remain dissolved therein. Such stabilization is desirable if the NGL product is to be transported or stored for later use, for example. In the embodiment depicted in FIG. 3, the second separation step, 212, is carried out in a simple phase separator or the like and the third separation step, 315, is carried out in a distillation column, generally operated as a deethanizer or demethanizer. Third separation step 315 produces an overhead third gas stream, 317, depleted in $C_{3+}$ hydrocarbons and a bottom third hydrocarbon liquid stream, 316, which forms the stabilized NGL product.

Third gas stream 317 may be combined with stream 219 as second gas mixture stream, 320, which forms the feed stream to membrane separation step 221. A residue stream, 224, that is enriched in $C_{3+}$ hydrocarbons relative to stream 320, is withdrawn from the feed side of the membrane. A permeate stream, 222, depleted in $C_{3+}$ hydrocarbons compared to stream 320, is withdrawn from the permeate side of the membrane.

Figure 4:
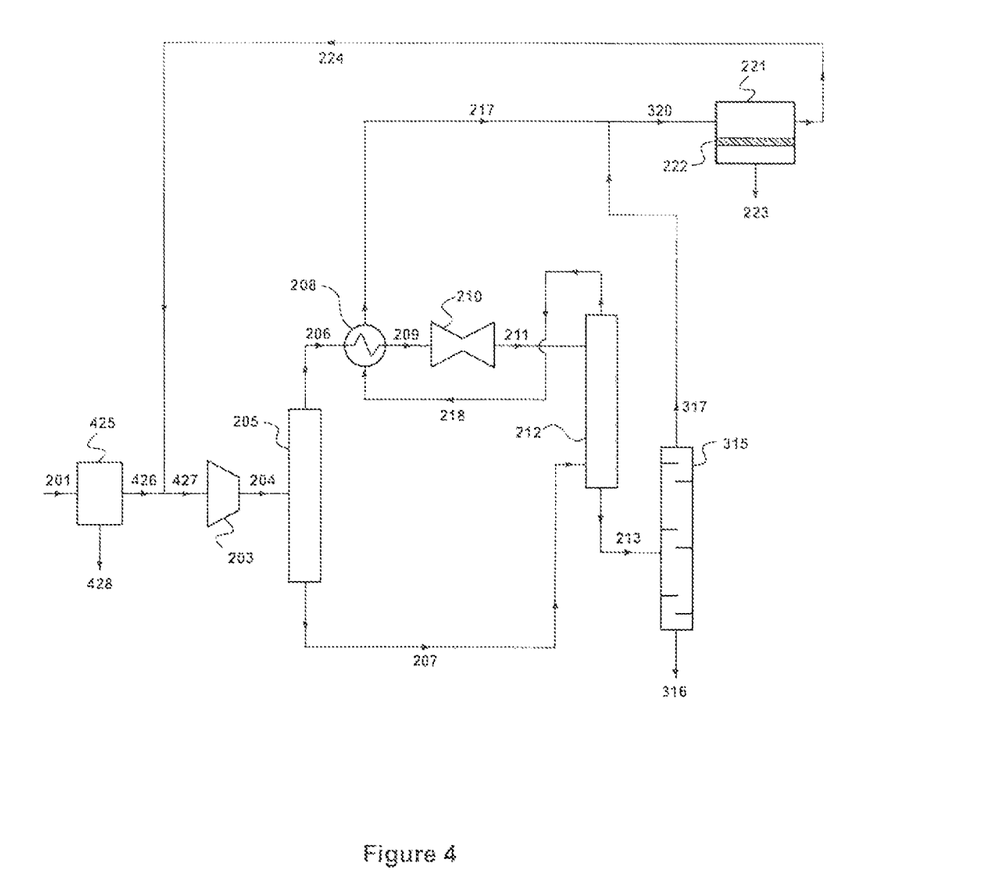
FIG. 4 is a schematic drawing showing an alternative embodiment of the invention of FIG. 3 with the addition of a dehydration unit.

Another embodiment of the NGL recovery process is shown in FIG. 4. This embodiment is similar to that of FIG. 3, except that an upstream dehydration step has been included as an explicit step in the process. (In the embodiments of FIGS. 2 and 3, dehydration was assumed to have taken place upstream of the process, or to be unnecessary for some reason).

Flare gas, 201, frequently contains a significant amount of water vapor or hydrates. These contaminants must be removed prior to the separation steps, to enable these steps to be operated at below freezing temperatures without clogging. In the embodiment shown in FIG. 4, flare gas 201 is directed to a dehydration step, 425, which removes a water-enriched stream, 428. Any type of dehydration unit known in the art may be used in this step. In a preferred embodiment, the dehydration unit is a molecular sieve.

A dehydrated gas stream, 426, is withdrawn from the dehydration unit of step 425 and is then combined with the recycled residue stream, 224, to produce a first gas mixture stream, 427. First gas mixture stream 427 is then sent through compression step 203.

Figure 5:
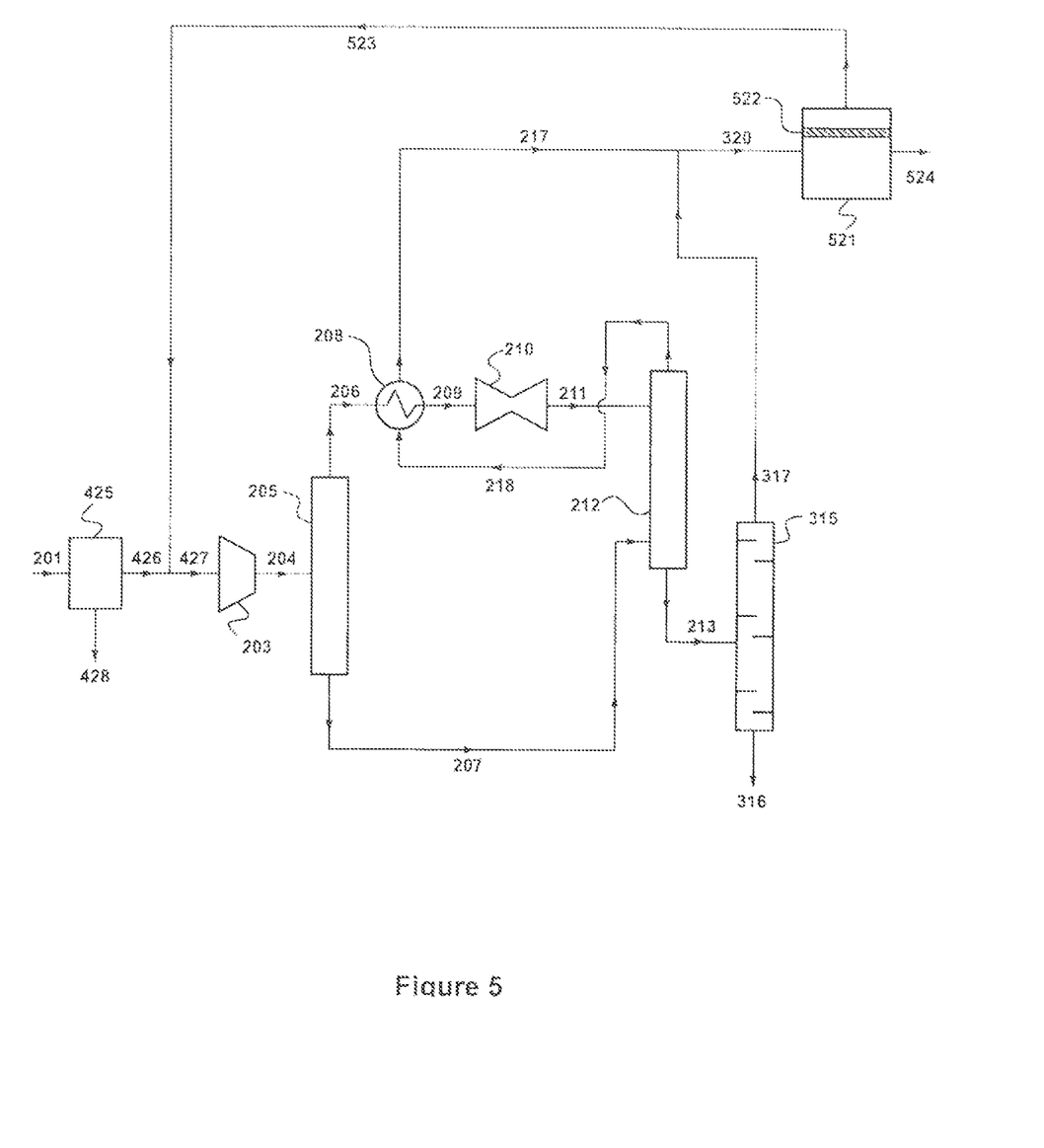
FIG. 5 is a schematic drawing showing an alternative embodiment of the invention of FIG. 4, but the membrane has a selective layer comprising a rubbery polymer.

A further embodiment of the NGL recovery process is shown in FIG. 5. This embodiment is similar to that of FIG. 4, but uses a methane-rejecting, rather than a methane-selective membrane.

Stream 320 is sent as a feed stream to a membrane separation step, 521. Any membrane with suitable performance properties may be used in the membrane separation step. The membrane may take the form of a homogeneous film, an integral asymmetric membrane, a multi-layer composite membrane, a membrane incorporating a gel or liquid layer or particulates, or any other form known in the art.

Membranes for use in separation step 521 may comprise a selective layer, 522, that may comprise any polymer that will preferentially permeate $C_{3+}$ hydrocarbons over methane. Preferably, these polymers are made from an elastomeric or rubbery polymer, examples of which include, but are not limited to, nitrile rubber, neoprene, polydimethylsiloxane (silicone rubber), chlorosulfonated polyethylene, polysilicone-carbonate copolymers, fluoroelastomers, etc. Silicone rubber is the most preferred material for separating $C_{3+}$ hydrocarbons from methane.

A residue stream, 524, that is depleted in $C_{3+}$ hydrocarbons relative to stream 320, is withdrawn from the feed side of the membrane. This stream can be used as fuel gas or flared. A permeate stream, 523, enriched in $C_{3+}$ hydrocarbons compared to stream 320, is withdrawn from the permeate side of the membrane. This stream represents a significant source of $C_{3+}$ hydrocarbons that is recycled back to the process prior to compression step 203. Stream 523 is combined with dehydrated stream 426 to produce a first gas mixture stream, 427, that is fed into the compressor of compression step, 203.

Figure 6:
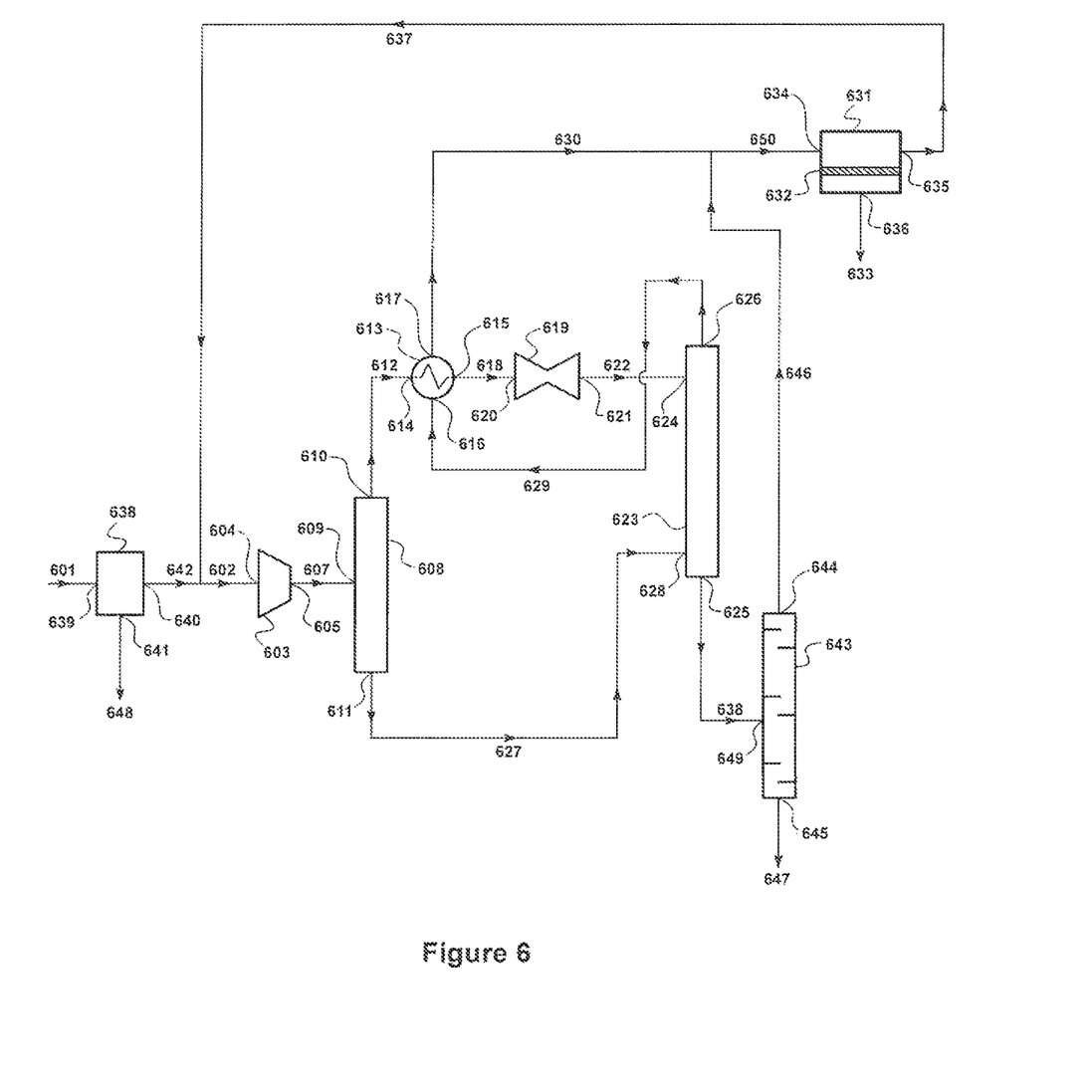
FIG. 6 is a schematic drawing showing a basic embodiment of an NGL recovery system of the present invention that includes a dehydration unit, a compressor, a first separation unit, a heat exchanger, a J-T valve, a second separation unit, a third separation unit, and a membrane.

FIG. 6 is a schematic drawing of a system for recovering NGL and methane. The system comprises a dehydration unit, 638, that includes a flare gas inlet, 639, a dehydrated stream outlet, 640, and a water-enriched stream outlet, 641.

In operation, a flare gas stream, 601, comprising at least methane and $C_{3+}$ hydrocarbons enters into a dehydration unit, 638, through a flare gas inlet, 639. A water-enriched stream 648, is withdrawn from the dehydration unit, 638, via the water-enriched stream outlet, 641. A dehydrated stream, 642, exits the dehydration unit, 638, from the dehydrated stream outlet, 640.

The compressor, 603, includes a gas mixture stream inlet, 604, that is in gas communication with the dehydration stream outlet, 640, and a residue stream outlet, 635. The dehydrated stream flows from the dehydration unit, is mixed with a residue stream, 637, and enters the compressor as gas mixture stream 602 through the gas mixture stream inlet, 604. The compressor, 603, also includes a compressed gas outlet, 605, that allows a compressed gas stream, 607, to be withdrawn.

The first separation unit, 608, includes a compressed gas stream inlet, 609, a first gas stream outlet, 610, and a first hydrocarbon liquid stream outlet, 611. The compressed gas stream inlet, 609, is in gas communication with compressed gas outlet, 605. The compressed gas stream inlet, 609, allows the compressed gas, 607, to enter the first separation unit, 608. The compressed gas, 607, is then separated into a first gas stream, 612, which is withdrawn from the first gas stream outlet, 610, and a first hydrocarbon liquid stream, 627, which is withdrawn from the first hydrocarbon liquid stream outlet, 611.

The heat-exchanger, 613, includes a first gas stream inlet, 614, a cooled gas stream outlet, 615, a second gas stream inlet, 616, and a heated gas stream outlet, 617. The first gas stream inlet, 614, is in gas communication with the first gas stream outlet, 610. The first gas stream inlet, 614, allows the first gas stream, 612, to enter into heat-exchanger 613, where it is cooled against a second gas stream, 629. The cooled gas stream outlet, 615, allows a cooled gas stream, 618, to exit the heat-exchanger, 613. The second gas stream inlet, 616, and the heated gas outlet, 617, are described in further detail below.

The J-T valve, 619, includes a J-T inlet, 620, and a J-T outlet, 621. The J-T inlet is in gas communication with the cooled gas stream outlet, 615. The cooled gas stream, 618, enters the J-T valve, 619, through J-T inlet 620. The J-T valve expands cooled gas stream, 618, to produce an expanded gas stream, 622, which is withdrawn via J-T outlet, 621.

The second separation unit, 623, includes an expanded gas inlet, 624, a second hydrocarbon liquid stream outlet, 625, a first hydrocarbon liquid stream inlet, 628, and a second gas stream outlet, 626. The expanded gas inlet, 624, is in gas communication with J-T valve 619 and the first hydrocarbon liquid stream inlet, 628, is in fluid communication with the first hydrocarbon liquid stream outlet, 611. The expanded gas stream, 622, and the first hydrocarbon liquid stream, 628, enter the second separation unit, 623, via inlets, 624, and 628, respectively. The second separation unit, 623, produces a second gas stream, 629, and a second hydrocarbon liquid stream, 638. The second gas stream, 629 exits unit 623 through second gas stream outlet, 626, and the second hydrocarbon liquid stream, 638, exits through the second hydrocarbon liquid stream outlet, 625.

As discussed above, heat exchanger 613 also comprises second gas stream inlet, 616, and a heated gas stream outlet, 617. The second gas stream inlet, 616, is in gas communication with the second gas stream outlet, 626. This allows for the second gas stream, 629, to flow from the second separation unit, 623, back through heat exchanger, 613. Stream 629 is heated by heat exchange against first gas stream 612. A heated gas stream, 630, is withdrawn from the heat exchanger, 617, through heated gas stream outlet, 617.

A third separation unit, 643, includes a second liquid hydrocarbon stream inlet, 649, a third hydrocarbon liquid stream outlet, 645, and a third gas stream outlet, 644. The second liquid hydrocarbon stream inlet, 649, is in fluid communication with second liquid hydrocarbon stream outlet, 625. The second liquid hydrocarbon stream, 638, enters the third separation unit, 643, through inlet, 649, and is separated into a third hydrocarbon liquid stream, 647, and a third gas stream, 646. The third gas stream, 646 exits unit 643 through third gas stream outlet, 644, and the third hydrocarbon liquid stream, 647, exits through the third hydrocarbon liquid stream outlet, 645.

The membrane, 631, comprises a feed inlet, 634, a permeate outlet, 636, and a residue outlet, 635. The feed inlet, 634, is in gas communication with the heated gas outlet, 617 of heat exchanger, 613, and third gas stream outlet 644. The residue outlet, 635, is in gas communication with the gas mixture stream inlet, 604, of the compressor, 603.

Feed inlet, 634, allows a mixture, 650, of the heated gas stream, 630, and the third gas stream, 646, to enter the membrane, 631, which comprises a selective layer, 632. In the embodiment shown in FIG. 6, the selective layer, 632, comprises a glassy polymer and preferentially removes methane from $C_{3+}$ hydrocarbons. The permeate stream, 633, is enriched in methane and exits the membrane through permeate outlet 636. The residue stream, 637, is depleted in methane and is withdrawn from the membrane via residue outlet 635.

In other embodiments, membrane selective layer 632 may comprise a rubbery polymer. In these cases, the membrane, 631, will comprise a permeate outlet, 633, that is in gas communication with the gas mixture stream inlet, 604, of compressor, 603.

The invention is now further described by the following examples, which are intended to be illustrative of the invention, but are not intended to limit the scope or underlying principles in any way.

EXAMPLES

Example 1. NGL Recovery Process Using Refrigeration According to FIG. 1 (not in Accordance with the Invention)

For comparison with the following examples, a calculation was performed in a low-temperature refrigeration process where none of the streams are treated by membrane separation. The process of FIG. 1 is described above. Feed stream 101 was assumed to have been dehydrated in step 102 using a molecular sieve, so that stream 103 contains essentially no water. The stream was assumed to be refrigerated to −40° F. in step 109.

The calculation was performed using differential element membrane code written at MTR and incorporated into a computer process simulation program (ChemCad 6.3, ChemStations, Austin, Tex.).

The results of the calculations are shown in Table 1:

TABLE 1

| | Stream Number | | | | | | | | | |
|---|---|---|---|---|---|---|---|---|---|---|
| | 103 Dry feed | 105 | 107 | 108 | 110 | 112 | 115 | 117 | 118 Fuel gas | 119 NGL |
| Temp F. | 100 | 234 | 100 | 100 | −40 | −38 | −38 | 44 | −27 | 155 |
| Pres psia | 65 | 200 | 200 | 200 | 198 | 198 | 198 | 280 | 198 | 285 |
| Total lbmol/h | 129.79 | 129.79 | 128.56 | 1.23 | 128.56 | 36.78 | 93.01 | 13 | 106.01 | 23.78 |
| Total lb/h | 3619 | 3619 | 3527 | 91.37 | 3527 | 1628 | 1991 | 376 | 2366 | 1252 |
| Total std L gpd | 24920 | 24920 | 24500 | 420 | 24500 | 9443 | 15477 | 2833 | 18310 | 6609 |
| Total std V MMscfd | 1.18 | 1.18 | 1.17 | 0.01 | 1.17 | 0.33 | 0.85 | 0.12 | 0.97 | 0.22 |
| | Component mole % | | | | | | | | | |
| Nitrogen | 8.78 | 8.78 | 8.86 | 0.24 | 8.86 | 0.38 | 12.1 | 1.08 | 10.75 | 0 |
| Methane | 50.23 | 50.23 | 50.67 | 3.77 | 50.67 | 9.61 | 66.29 | 27.2 | 61.5 | 0 |
| Carbon Dioxide | 0.58 | 0.58 | 0.58 | 0.1 | 0.58 | 0.37 | 0.66 | 1.05 | 0.71 | 0 |
| Hydrogen Sulfide | 0 | 0 | 0 | 0 | 0 | 0.01 | 0 | 0.01 | 0 | 0 |
| Ethane | 18.12 | 18.12 | 18.24 | 6.24 | 18.24 | 24.09 | 15.76 | 54.47 | 20.51 | 7.5 |
| Propane | 15.02 | 15.02 | 15.01 | 15.75 | 15.01 | 40.92 | 4.77 | 14.44 | 5.96 | 55.39 |
| C4+ Hydrocarbons | 7.26 | 7.26 | 6.62 | 73.89 | 6.62 | 24.60 | 0.4 | 1.73 | 0.56 | 37.11 |
| Water | 0 | 0 | 0 | 0 | 0 | 0 | 0 | 0.01 | 0 | 0 |

With compression to 200 psia and refrigeration to −40° F., the process recovers about 80 mol % of the $C_{3+}$ hydrocarbons from the flare gas feed stream.

Example 2. NGL Recovery Process in Accordance with the Invention of FIG. 2 or 3

A calculation was performed to model the performance of the process of FIG. 2 or FIG. 3 in recovering an NGL stream. For the purposes of this calculation, it was assumed that no dehydration is used, so that all streams must remain well above the temperature of ice or hydrate formation. Thus, the J-T expansion step was assumed to lower the pressure of the gas stream from about 600 psia by only about half, to 325 psia. As a result, the temperature of the expanded stream, 211, only fell to about 60° F. (about 15° C.). The results of the calculations are shown in Table 2.

TABLE 2

| | Stream Number | | | | | | | | | |
|---|---|---|---|---|---|---|---|---|---|---|
| | 201 Feed | 204 | 209 | 211 | 207 | 213 NGL* | 316 NGL** | 320 | 223 Fuel gas | 224 |
| Temp F. | 100 | 100 | 90 | 61 | 100 | 63 | 100 | 84 | 79 | 76 |
| Pres psia | 65 | 600 | 598 | 325 | 600 | 325 | 275 | 320 | 65 | 286 |
| Total lbmol/h | 132 | 380 | 357 | 357 | 23 | 25 | 19 | 359 | 108 | 251 |
| Total lb/h | 3653 | 10785 | 9801 | 9801 | 985 | 1229 | 1048 | 9709 | 2497 | 7204 |
| Total std L gpd | 25015 | 77513 | 69976 | 69976 | 5538 | 6780 | 5436 | 7002 | 18936 | 51009 |
| Total std V MMscfd | 1.20 | 3.46 | 3.25 | 3.25 | 0.21 | 0.23 | 0.17 | 3.27 | 0.98 | 2.28 |
| | Component mole % | | | | | | | | | |
| Nitrogen | 8.65 | 5.75 | 6.07 | 6.07 | 0.68 | 0.33 | 0 | 6.08 | 10.43 | 4.21 |
| Methane | 49.49 | 44.57 | 46.65 | 46.65 | 11.58 | 7.20 | 0 | 47.15 | 59.21 | 41.95 |
| Carbon Dioxide | 0.57 | 0.30 | 0.31 | 0.31 | 0.14 | 0.11 | 0 | 0.32 | 0.69 | 0.16 |
| Hydrogen Sulfide | 0 | 0 | 0 | 0 | 0 | 0 | 0 | 0 | 0 | 0 |
| Ethane | 17.86 | 23.42 | 23.70 | 23.70 | 18.96 | 17.08 | 7.0 | 24.40 | 19.84 | 26.37 |
| Propane | 14.80 | 19.92 | 18.91 | 18.91 | 35.98 | 41.26 | 48.99 | 18.46 | 8.78 | 22.64 |
| C4+ Hydrocarbons | 7.15 | 5.50 | 4.18 | 4.18 | 26.43 | 33.98 | 44.0 | 3.47 | 0.80 | 4.62 |
| Water | 1.48 | 0.54 | 0.18 | 0.18 | 6.23 | 0.04 | 0 | 0.10 | 0.24 | 0.04 |

*Unstabilized NGL product as in FIG. 2
**Stabilized NGL product as in FIG. 3

Using the J-T valve and membrane combination, the process achieved about 65 mol % of heavier hydrocarbons recovery in the NGL product stream, 213, even though the gas was only cooled to about 15° C.

Example 3. NGL Recovery Process in Accordance with the Invention of FIG. 4

A calculation was performed to model the performance of the process of FIG. 4 in recovering a NGL stream. The flare gas stream was assumed to be dehydrated, compressed to 1,200 psia and cooled to 21° F. (−6° C.) by expansion to 325 psia. The results of the calculations are shown in Table 3.

TABLE 3

| | Stream Number | | | | | | | |
|---|---|---|---|---|---|---|---|---|
| | 201 | 204 | 206 | 207 | 209 | 211 | 218 | 219 |
| Temp F. | 100 | 441 | 100 | 100 | 70 | 11 | 21 | 90 |
| Pres psia | 65 | 1200 | 1200 | 1200 | 1198 | 325 | 325 | 323 |
| Enth hp | −1854 | −2148 | −1927 | −687 | −1971 | −1971 | −1848 | −1804 |
| Vapor mole frac. | 1 | 1 | 1 | 0 | 1 | 1 | 1 | 1 |
| Total lbmol/h | 132 | 178 | 140 | 38 | 140 | 140 | 141 | 141 |
| Total lb/h | 3653 | 5015 | 3624 | 1391 | 3624 | 3624 | 3343 | 3343 |
| Total std L gpd | 25015 | 35012 | 26264 | 8748 | 26264 | 26264 | 25327 | 25327 |
| Total std V MMscfd | 1.2 | 1.62 | 1.27 | 0.35 | 1.27 | 1.27 | 1.28 | 1.28 |
| | Component mole % | | | | | | | |
| Nitrogen | 8.65 | 7.07 | 8.25 | 2.78 | 8.25 | 8.25 | 8.85 | 8.85 |
| Methane | 49.49 | 47.16 | 52.15 | 28.92 | 52.15 | 52.15 | 57.15 | 57.15 |
| Carbon Dioxide | 0.57 | 0.43 | 0.45 | 0.37 | 0.45 | 0.45 | 0.49 | 0.49 |
| Hydrogen Sulfide | 0.00 | 0.00 | 0.00 | 0.00 | 0.00 | 0.00 | 0.00 | 0.00 |
| Ethane | 17.86 | 22.06 | 21.39 | 24.52 | 21.39 | 21.39 | 21.80 | 21.80 |
| Propane | 14.80 | 17.02 | 14.11 | 27.65 | 14.11 | 14.11 | 10.45 | 10.45 |
| C4+ Hydrocarbons | 7.15 | 6.24 | 3.64 | 15.75 | 3.64 | 3.64 | 1.26 | 1.26 |
| Water | 1.48 | 0.01 | 0.01 | 0.00 | 0.01 | 0.01 | 0.01 | 0.01 |

| | Stream Number | | | | | | | |
|---|---|---|---|---|---|---|---|---|
| | 223 | 224 | 314 | 316 | 317 | 320 | 425 | 427 | 428 |
| Temp F. | 79 | 71 | 21 | 171 | 67 | 87 | 100 | 83 | 100 |
| Pres psia | 65 | 316 | 325 | 325 | 320 | 320 | 65 | 65 | 65 |
| Enth hp | −1306 | −714 | −810 | −519 | −217 | −2021 | −1775 | −2482 | −93 |
| Vapor mole frac. | 1 | 1 | 0 | 0 | 1 | 1 | 1 | 1 | 0 |
| Total lbmol/h | 106 | 49 | 38 | 23 | 14 | 155 | 130 | 178 | 2 |

TABLE 3-continued

| | | | | | | | | | |
|---|---|---|---|---|---|---|---|---|---|
| Total lb/h | 2361 | 1411 | 1673 | 1244 | 430 | 3772 | 3618 | 5015 | 35 |
| Total std L gpd | 18270 | 10200 | 9691 | 6545 | 3147 | 28474 | 24915 | 35012 | 100 |
| Total std V MMscfd | 0.96 | 0.45 | 0.34 | 0.21 | 0.13 | 1.41 | 1.18 | 1.62 | 0.02 |
| Component mole % | | | | | | | | | |
| Nitrogen | 10.76 | 2.50 | 0.47 | 0.00 | 1.25 | 8.15 | 8.78 | 7.07 | 0.00 |
| Methane | 61.43 | 38.94 | 10.02 | 0.00 | 26.47 | 54.31 | 50.23 | 47.16 | 0.00 |
| Carbon Dioxide | 0.71 | 0.05 | 0.23 | 0.00 | 0.60 | 0.50 | 0.58 | 0.43 | 0.00 |
| Hydrogen Sulfide | 0.00 | 0.00 | 0.00 | 0.00 | 0.01 | 0.00 | 0.00 | 0.00 | 0.00 |
| Ethane | 20.53 | 32.60 | 23.04 | 7.00 | 49.35 | 24.35 | 18.12 | 22.06 | 0.00 |
| Propane | 6.15 | 22.38 | 41.46 | 54.79 | 19.59 | 11.29 | 15.02 | 17.02 | 0.00 |
| C4+ Hydrocarbons | 0.40 | 3.53 | 24.77 | 38.22 | 2.72 | 1.39 | 7.26 | 6.24 | 0.00 |
| Water | 0.01 | 0.00 | 0.00 | 0.00 | 0.01 | 0.01 | 0.01 | 0.01 | 100 |

In this case, the process of the invention recovers an NGL product containing about 77 mol % of the heavier hydrocarbons from the flare gas.

Example 4. NGL Recovery Process in Accordance with the Invention of FIG. 5

A calculation was performed to model the performance of the process of FIG. 5 in recovering a NGL stream. In this case, it was assumed that a membrane selective in favor of heavier hydrocarbons over methane was used. The results of the calculations are shown in Table 4.

Using a dehydration unit with a J-T valve and a membrane with a selective layer comprising a rubbery polymer achieves about 80 mol % recovery of heavier hydrocarbons in the NGL product stream.

We claim:
1. A system for recovering natural gas liquids from flare gas, comprising:
   (a) a compressor including a gas mixture stream inlet and a compressed gas outlet;
   (b) a first separation unit including a compressed gas inlet, a first hydrocarbon liquid stream outlet, and a first gas

TABLE 4

| | Stream Name | | | | | | | |
|---|---|---|---|---|---|---|---|---|
| | 201 | 204 | 206 | 207 | 209 | 218 | 219 | 314 |
| Temp F. | 100 | 451 | 100 | 100 | 75 | 17 | 85 | 17 |
| Pres psia | 65 | 1200 | 1200 | 1200 | 1198 | 350 | 348 | 350 |
| Enth hp | −1854 | −3488 | −3813 | −392 | −3887 | −3219 | −3145 | −1059 |
| Vapor mole frac. | 1 | 1 | 1 | 0 | 1 | 1 | 1 | 0 |
| Total lbmol/h | 132 | 285 | 263 | 22 | 263 | 233 | 233 | 52 |
| Total lb/h | 3653 | 7697 | 6929 | 768 | 6929 | 5583 | 5583 | 2114 |
| Total std L gpd | 25015 | 56108 | 51092 | 5017 | 51092 | 43232 | 43232 | 12881 |
| Total std V MMscfd | 1.20 | 2.59 | 2.39 | 0.20 | 2.39 | 2.12 | 2.12 | 0.47 |
| Component mole % | | | | | | | | |
| Nitrogen | 8.65 | 5.28 | 5.54 | 2.17 | 5.54 | 6.36 | 6.36 | 0.39 |
| Methane | 49.49 | 46.44 | 47.94 | 28.70 | 47.94 | 54.33 | 54.33 | 10.73 |
| Carbon Dioxide | 0.57 | 0.99 | 1.00 | 0.83 | 1.00 | 1.08 | 1.08 | 0.56 |
| Hydrogen Sulfide | 0.00 | 0.01 | 0.01 | 0.01 | 0.01 | 0.01 | 0.01 | 0.01 |
| Ethane | 17.86 | 29.54 | 29.26 | 32.80 | 29.26 | 28.73 | 28.73 | 33.22 |
| Propane | 14.80 | 13.64 | 12.86 | 22.91 | 12.86 | 8.57 | 8.57 | 36.57 |
| C4+ Hydrocarbons | 7.15 | 4.09 | 3.37 | 12.58 | 3.37 | 0.90 | 0.90 | 18.51 |
| Water | 1.48 | 0.01 | 0.01 | 0.01 | 0.01 | 0.01 | 0.01 | 0.01 |

| | Stream Name | | | | | | | |
|---|---|---|---|---|---|---|---|---|
| | 316 | 317 | 320 | 426 | 427 | 428 | 523 | 524 |
| Temp F. | 160 | 53 | 77 | 100 | 82 | 100 | 65 | 53 |
| Pres psia | 305 | 300 | 300 | 65 | 65 | 65 | 65 | 296 |
| Enth hp | −567 | −397 | −3542 | −1775 | −4026 | −94 | −2274 | −1268 |
| Vapor mole frac. | 0 | 1 | 1 | 1 | 1 | 0 | 1 | 1 |
| Total lbmol/h | 26 | 26 | 259 | 130 | 285 | 2 | 157 | 102 |
| Total lb/h | 1341 | 773 | 6357 | 3618 | 7697 | 35 | 4121 | 2236 |
| Total std L gpd | 7115 | 5766 | 48997 | 24914 | 56108 | 101 | 31509 | 17484 |
| Total std V MMscfd | 0.23 | 0.23 | 2.36 | 1.18 | 2.59 | 0.02 | 1.43 | 0.93 |
| Component mole % | | | | | | | | |
| Nitrogen | 0.00 | 0.79 | 5.80 | 8.78 | 5.28 | 0.00 | 2.35 | 11.09 |
| Methane | 0.00 | 21.45 | 51.05 | 50.23 | 46.44 | 0.00 | 43.27 | 62.97 |
| Carbon Dioxide | 0.00 | 1.12 | 1.09 | 0.58 | 0.99 | 0.00 | 1.33 | 0.71 |
| Hydrogen Sulfide | 0.00 | 0.02 | 0.01 | 0.00 | 0.01 | 0.00 | 0.01 | 0.00 |
| Ethane | 7.50 | 58.92 | 31.74 | 18.12 | 29.54 | 0.00 | 39.10 | 20.47 |
| Propane | 57.31 | 15.85 | 9.30 | 15.02 | 13.64 | 0.00 | 12.49 | 4.42 |
| C4+ Hydrocarbons | 35.19 | 1.85 | 1.00 | 7.26 | 4.09 | 0.00 | 1.44 | 0.32 |
| Water | 0.00 | 0.02 | 0.01 | 0.00 | 0.01 | 100.00 | 0.02 | 0.00 | stream outlet, wherein the compressed gas inlet is in gas communication with the compressed gas outlet;

(c) a heat-exchanger including a first gas stream inlet, a cooled gas stream outlet, a second gas stream inlet, and a heated gas stream outlet, wherein the first gas stream inlet is in gas communication with the first gas stream outlet of the first separation unit;

(d) a Joule-Thomson (J-T) valve including a J-T inlet and a J-T outlet, wherein the J-T inlet is in gas communication with the cooled gas stream outlet of the heat-exchanger;

(e) a second separation unit including an expanded gas inlet, a second hydrocarbon liquid stream outlet, and a second gas stream outlet, wherein the expanded gas stream inlet is in gas communication with the J-T outlet of the J-T valve, wherein the second gas stream outlet is in gas communication with the second gas stream inlet of the heat-exchanger;

(f) a third separation unit including a second hydrocarbon liquid stream inlet, a third gas stream outlet, and a third hydrocarbon liquid stream outlet, wherein the second hydrocarbon liquid stream inlet is in fluid communication with the second hydrocarbon liquid outlet of the second separation unit; and

(g) a membrane unit including a feed side and a permeate side, wherein the feed side is in gas communication with the heated gas stream outlet of the heat-exchanger and the third gas stream outlet of the third separation unit, and wherein the feed side is also in gas communication with the gas mixture stream inlet of the compressor.

2. The system of claim 1, further comprising a dehydration unit, including a flare gas inlet, a hydrate-enriched stream outlet, and a dehydrated stream outlet, wherein the gas mixture stream inlet of the compressor is in gas communication with the dehydrated stream outlet.

3. The system of claim 1, wherein the second separation unit is a distillation column.

4. The system of claim 1, wherein the third separation unit is a distillation column.

5. The system of claim 1, wherein the membrane unit comprises a membrane comprising a polymer having the formula:

where x and y represented the relative proportions of the dioxole and the tetrafluroethylene blocks, such that x+y=1, and where x>0 and y>0.

6. The system of claim 1, wherein the permeate stream is enriched in methane.

7. The system of claim 6, wherein the permeate stream is sent as fuel to a fuel user.

8. The system of claim 7, wherein the fuel user comprises power generation equipment.

9. The system of claim 7, wherein fuel user is a gas engine.

10. The system of claim 7, wherein fuel user drives the compressor in step (a).

11. The system of claim 2, wherein the dehydration unit is a molecular sieve.

12. The system of claim 1, wherein the first gas stream comprises a hydrate inhibiting chemical.

13. The system of claim 12, wherein the hydrate inhibiting chemical is methanol.

14. A system for recovering natural gas liquids from flare gas, comprising:

(a) a compressor including a gas mixture stream inlet and a compressed gas outlet;

(b) a first separation unit including a compressed gas inlet, a first hydrocarbon liquid stream outlet, and first gas stream outlet, wherein the compressed gas inlet is in gas communication with the compressed gas outlet;

(c) a heat-exchanger including a first gas stream inlet, a cooled gas stream outlet, a second gas stream inlet, and a heated gas stream outlet, wherein the first gas stream inlet is in gas communication with the first gas stream outlet of the first separation unit;

(d) a Joule-Thomson (J-T) valve including a J-T inlet and a J-T outlet, wherein the J-T inlet is in gas communication with the cooled gas stream outlet of the heat-exchanger;

(e) a second separation unit including an expanded gas inlet, a second hydrocarbon liquid stream outlet, and a second gas stream outlet, wherein the expanded gas stream inlet is in gas communication with the J-T outlet of the J-T valve, wherein the second gas stream outlet is in gas communication with the second gas stream inlet of the heat-exchanger;

(f) a third separation unit including a second hydrocarbon liquid stream inlet, a third gas stream outlet, and a third hydrocarbon liquid stream outlet, wherein the second hydrocarbon liquid stream inlet is in fluid communication with the second hydrocarbon liquid outlet of the second separation unit; and

(g) a membrane unit including a feed side and a permeate side, wherein the feed side is in gas communication with the heated gas stream outlet of the heat-exchanger and the third gas stream outlet of the third separation unit, and wherein the permeate side is in further gas communication with the gas mixture stream inlet of the compressor.

15. The system of claim 14, further comprising a dehydration unit including a flare gas inlet, a water-enriched stream outlet, and a dehydrated stream outlet, wherein the gas mixture stream inlet of the compressor is in gas communication with the dehydrated stream.

16. The system of claim 14, wherein the second separation unit is a distillation column.

17. The system of claim 14, wherein the third separation unit is a distillation column.

18. The system of claim 14, wherein the membrane unit comprises a membrane comprising a polymer having the formula:

where x and y represented the relative proportions of the dioxole and the tetrafluroethylene blocks, such that x+y=1, and where x>0 and y>0.

19. The system of claim 14, wherein the permeate stream is enriched in methane.

20. The system of claim 19, wherein the permeate stream is sent as fuel to a fuel user.

21. The system of claim 20, wherein the fuel user comprises power generation equipment.

22. The system of claim 20, wherein fuel user is a gas engine.

23. The system of claim 20, wherein fuel user drives the compressor in step (a).

24. The system of claim 15, wherein the dehydration unit is a molecular sieve.

25. The system of claim 14, wherein the first gas stream comprises a hydrate inhibiting chemical.

26. The system of claim 25, wherein the hydrate inhibiting chemical is methanol.

* * * * *